(12) United States Patent
Roth et al.

(10) Patent No.: US 8,165,364 B2
(45) Date of Patent: Apr. 24, 2012

(54) TEMPERATURE MANAGEMENT FOR ULTRASOUND IMAGING AT HIGH FRAME RATES

(75) Inventors: Scott L. Roth, East Hills, NY (US); Edward Paul Harhen, Duxbury, MA (US); Harold M. Hastings, Garden City, NY (US); Nicolas Heron, New York, NY (US)

(73) Assignee: Imacor Inc., Uniondale, NY (US)

( * ) Notice: Subject to any disclaimer, the term of this patent is extended or adjusted under 35 U.S.C. 154(b) by 999 days.

(21) Appl. No.: 12/129,912

(22) Filed: May 30, 2008

(65) Prior Publication Data

US 2008/0298654 A1   Dec. 4, 2008

Related U.S. Application Data

(60) Provisional application No. 60/941,480, filed on Jun. 1, 2007.

(51) Int. Cl.
  *G06K 9/00* (2006.01)
(52) U.S. Cl. .................. 382/128; 382/200; 382/131
(58) Field of Classification Search .................. None
  See application file for complete search history.

(56) References Cited

U.S. PATENT DOCUMENTS

| 6,056,691 | A | 5/2000 | Urbano et al. |
| 6,083,168 | A * | 7/2000 | Hossack et al. ............ 600/443 |
| 6,542,846 | B1 | 4/2003 | Miller |
| 6,663,578 | B1 | 12/2003 | Salgo |
| 6,709,392 | B1 | 3/2004 | Salgo |
| 7,678,048 | B1 * | 3/2010 | Urbano et al. ............ 600/437 |
| 2003/0028113 | A1 | 2/2003 | Gilbert |
| 2003/0045795 | A1 | 3/2003 | Bjaerum |
| 2006/0165179 | A1 * | 7/2006 | Feuer et al. ............ 375/240.18 |
| 2007/0083121 | A1 | 4/2007 | Hastings |

FOREIGN PATENT DOCUMENTS

| EP | 1614386 | 1/2006 |
| WO | WO 2006/023984 | 3/2006 |
| WO | WO 2007/000680 | 1/2007 |

OTHER PUBLICATIONS

International Search Report from corresponding application PCT/US2008/065282.

* cited by examiner

*Primary Examiner* — Melissa Koval
*Assistant Examiner* — Trung Nguyen
(74) *Attorney, Agent, or Firm* — Proskauer

(57) ABSTRACT

To keep the temperature of an ultrasound probe down, the probe is operated at a low frame rate (with correspondingly low heat generation) for the vast majority of time. Probe operation is only switched to the high frame rate temporarily at times when high temporal resolution is needed, preferably under operator control. The probe is only operated at the high frame rate for a short period of time, during which a burst of images with high temporal resolution is obtained. After capturing the short burst of images, the frame rate is cut back, which reduces the generation of heat.

18 Claims, 3 Drawing Sheets

TEMPERATURE MANAGEMENT FOR ULTRASOUND IMAGING AT HIGH FRAME RATES

CROSS REFERENCE TO RELATED APPLICATIONS

This application claims the benefit of U.S. provisional application 60/941,480, filed Jun. 1, 2007.

BACKGROUND

One conventional approach to monitoring heart function is transesophageal echocardiography (TEE), in which a probe containing an ultrasound transducer is inserted into the esophagus and positioned so that the transducer is near the patient's heart. The probe is then used to capture video images of the heart in real time, which are typically displayed on a video monitor. Conventional TEE probes typically measure between 10-15 mm in diameter (for adults). Because of this large diameter, conventional TEE often requires anesthesia, can significantly threaten the airway, and is not well suited for long-term monitoring of the heart. More recently, smaller TEE probes that permit long term monitoring and eliminate or reduce the need for anesthesia have been developed, as disclosed in US2005/0143657 (application Ser. No. 10/996,816, filed Nov. 24, 2004).

Under certain circumstances, operating a TEE probe at a high frame rate can cause the probe's temperature to increase by an undesirable amount. This can be particularly problematic with smaller probes, where less surface area is available for dissipation of the applied power.

SUMMARY

To keep the temperature of the ultrasound probe down, the probe is operated at a low frame rate (with correspondingly low heat generation) for the vast majority of time. Probe operation is only switched to the high frame rate temporarily at times when high temporal resolution is needed, and the probe is only operated at the high frame rate for a short period of time. During that time, a burst of images with high temporal resolution is obtained. After capturing the short burst of images, the frame rate is cut back, which reduces the generation of heat.

DETAILED DESCRIPTION OF THE PREFERRED EMBODIMENTS

All other things being equal, the temperature rise ($\Delta T$) of an ultrasound probe is proportional to the frame rate of the images. Heat management in ultrasound probes may therefore be implemented by switching the image-capture frame rate between two modes: a first mode with a high frame rate, for use at times when that high frame rate is required for the imaging task at hand, and a second mode with a low frame rate for use at times when that high frame rate is not required. Optionally, a third mode with an even lower frame rate (or a frame rate of zero) may be used to allow the probe to cool down faster after it is operated in the first mode.

For TEE imaging of the heart, a frame rate of 50 frames per second (fps) is suitable because that frame rate is fast enough for high speed applications (e.g., visualizing which portion of the heart is contracting late in a cardiac resync therapy application), yet slow enough for "speckle" noise from the blood to re-randomize (thereby reducing the impact of speckle noise on the image). However, with a small TEE probe (e.g., with a transducer with a surface area on the order of 200 mm$^2$), operating the probe at 50 fps continuously can cause an undesirable increase in the probe's temperature.

Figure 1:
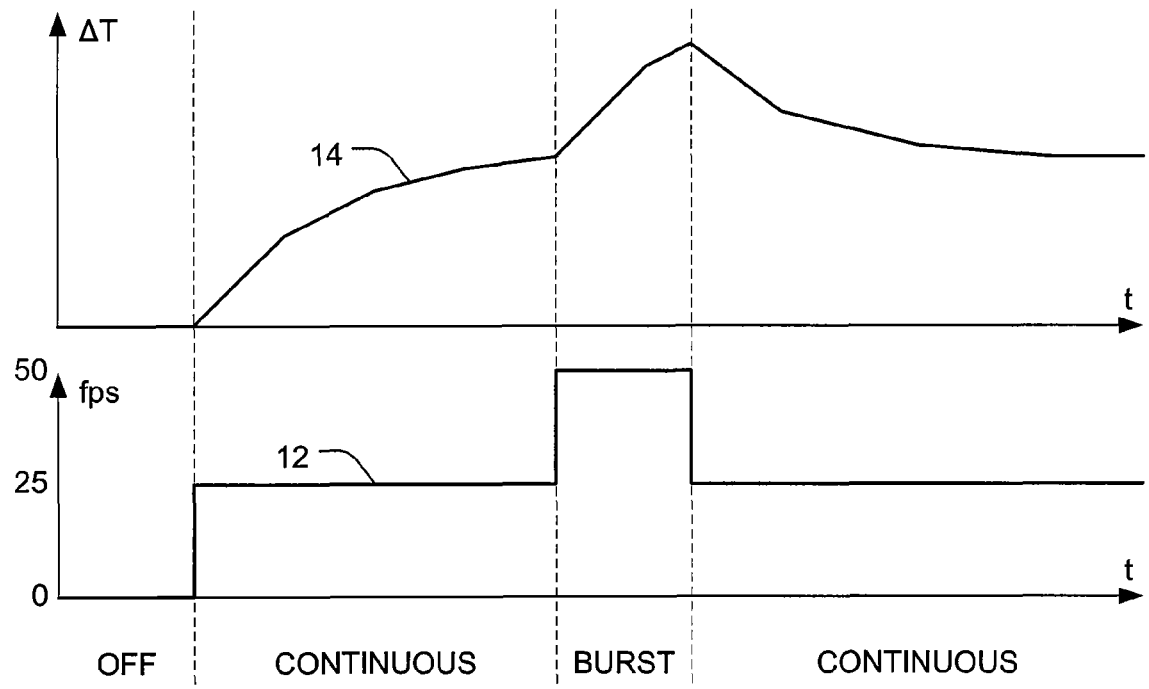
FIG. 1 is a graph depicting a first approach for reducing the probe temperature.

In these applications, however, continuous operation at the high frame rate can be avoided by operating the probe at a lower frame rate (e.g., on the order of 25 fps), during the portion of the procedure when the probe is being positioned. Preferably, this lower frame rate is slow enough such that $\Delta T$ drops to the point where the probe can be safely operated continuously. This mode of operation is referred to herein as the "continuous" mode. Then, after the probe is positioned at its desired location, a clip of images are captured at the higher frame rate (e.g., on the order of 50 fps) for a short period of time (e.g., 3 seconds). This mode of operation is referred to herein as the "burst" mode. After the high speed burst, operation returns to the continuous mode. The changing frame rate in this mode of operation is depicted by the lower trace 12 in FIG. 1, and the resulting temperature rise $\Delta T$ is depicted by the upper trace 14.

Figure 2:
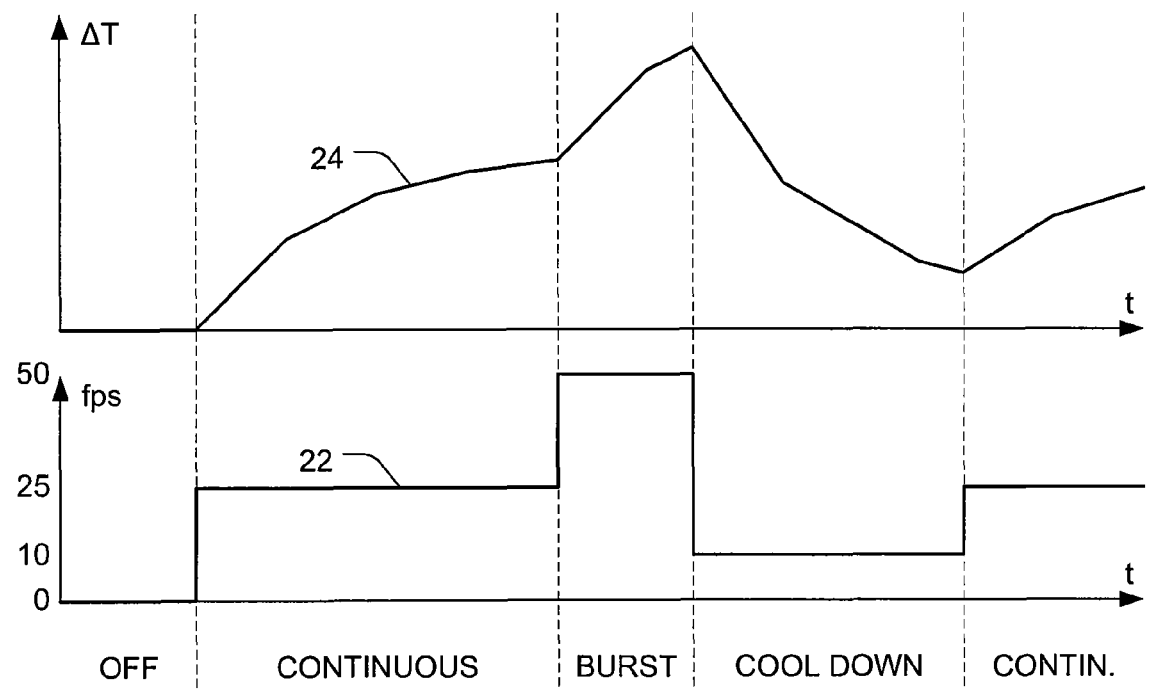
FIG. 2 is a graph depicting a second approach for reducing the probe temperature.

Optionally, a low frame rate "cool down" mode may be added after the burst mode to speed up the cooling of the probe, as illustrated in FIG. 2. This cool down mode may be implemented either by slowing down the frame rate to less than the frame rate of the continuous mode (e.g., on the order of 10 fps), or by completely stopping the image capture process (not shown). Preferably, if image capture is completely stopped, a suitable indication is displayed via an appropriate user interface, so the operator will not think that the system is malfunctioning. In addition, any pauses in imaging should preferably be short (e.g., less than 10 seconds) to avoid annoying the operator. Once the probe has cooled sufficiently, another high speed burst may be performed. The changing frame rate in this mode of operation is depicted by the lower trace 22 in FIG. 2, and the resulting temperature rise $\Delta T$ is depicted by the upper trace 24. Preferably, all three of the frame rates occur during the same imaging session of the same subject (e.g., they all occur within less than a minute, preferably within less than 30 seconds, and more preferably within 15 seconds), one after the other, either with no breaks or very short breaks between the various frame rates.

In one example, the temperature rise of a probe operating continuously at 24 fps was about 3.2° C. (measured with a tissue phantom). Since the thermal time constant of ultrasound probes is relatively large, a three second high speed burst does not cause a significant instantaneous increase in temperature. As long as the high speed bursts are relatively short (e.g., less than five seconds, and more preferably on the order of three seconds) and the cool-down periods are sufficiently long, $\Delta T_{MAX}$ will never be too much higher than the $\Delta T$ that is associated with continuous operation.

All other things being equal, power and thus relative heat generation is directly proportional to frame rate. Thus, operating at 50 fps will generate 50/24=2.08 times as much heat as in the 24 fps normal mode, and operating in a 10 fps cooldown mode will generate 10/24=0.41 times as much heat as in the 24 fps normal mode. The cool down period is preferably sufficiently long and sufficiently close enough in time to the high speed burst so as to compensate for the entire temperature rise caused by operating at the high frame rate. This can be accomplished by keeping the total frame count below the frame count associated with the normal continuous frame rate. For example, in a system operating continuously at 24 fps, there would be 288 frames in a 12 second interval. In contrast, doing a three second burst at 50 fps followed by a nine second cool-down at 10 fps would result in a lower frame count of (50×3)+(10×9)=240 frames in 12 seconds. As a result, the temperature at the end of the burst and cool-down cycle should be lower than the steady-state temperature for the continuous mode. In another example, doing a three second bust at 50 fps followed by a seven second cool-down at 10 fps, followed by another similar burst and cool-down would result in a lower total frame count (440) than continuous operation at 24 fps for 20 seconds (which yields in a frame count of 480).

The above-described techniques are particularly useful to achieve compliance with the FDA's ALARA ("as low as reasonably achievable") principle for heating. This is particularly important for applications in which the probe remains installed in the patient for long periods of time (e.g., over 6 hours) to minimize negative consequences from long term heating by only capturing short burst at a high frame rate as required, and otherwise running at a low frame rate. Note that a 3 second burst is sufficiently long to capture two complete cardiac cycles when the heart is beating at 60 bpm.

The above-described techniques are also useful for keeping the temperature rise below the maximum temperature rise of 6° C. recommended under IEC60601, and more preferably below 4° C.

Figure 4:
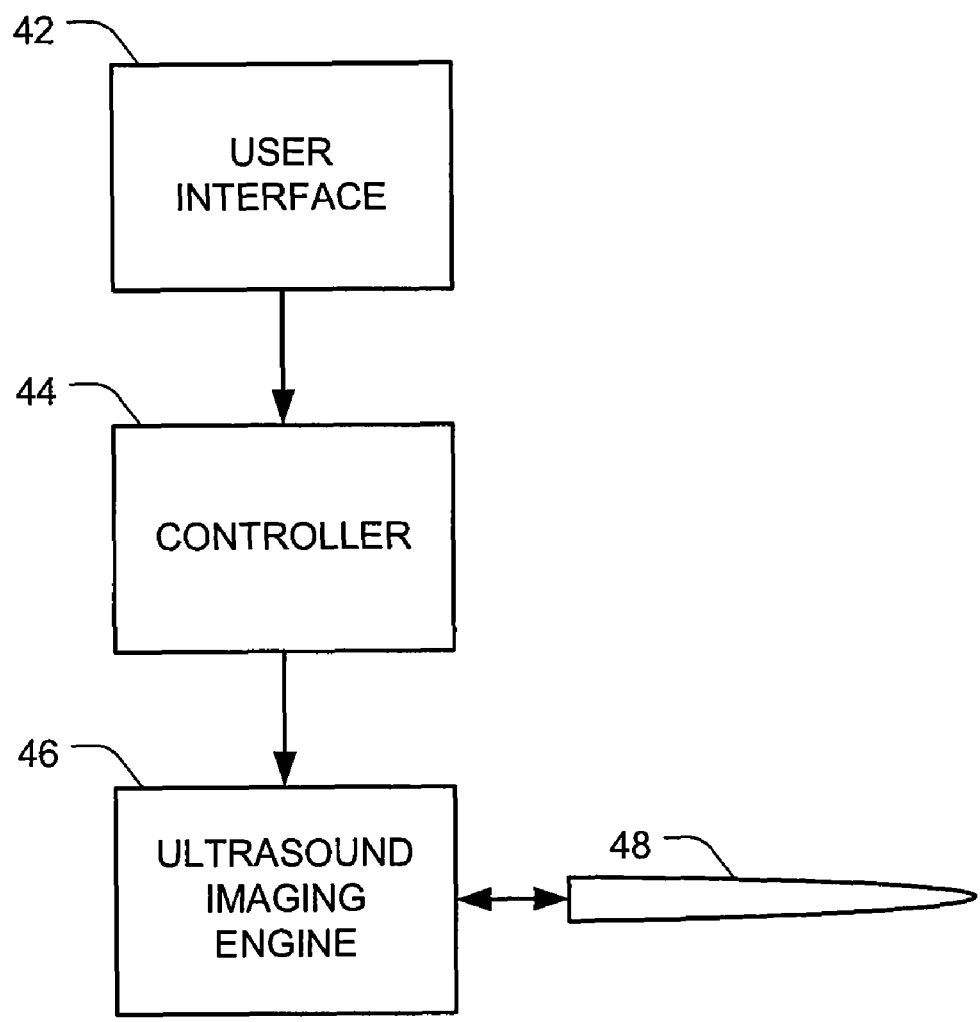
FIG. 4 is a block diagram of a system for implementing the thermal management approaches described herein.

FIG. 4 is a block diagram of a suitable system for implementing the thermal management approaches described above. The ultrasound imaging engine 46 drives the transducer in the probe 48, receives return signals from the transducer, and converts those returns signals into an image that is ultimately displayed on a suitable display. The implementation of ultrasound imaging engines with digital controls for various parameters such as frame rate, sector angle, and lines per frame is well known to persons skilled in the relevant arts; and control over such imaging engines may be achieved, for example, by writing appropriate control words to the appropriate control addresses, also in a manner well known to persons skilled in the relevant arts.

The controller 44 control sends commands to the ultrasound engine 46 via a suitable interface (e.g., a digital bus) to change the frame rate in accordance with the approaches described above in connection with FIGS. 1 and 2. Optionally, the resolution of the image may also be increased during the high speed burst mode (e.g., by shooting 42 lines per frame in the normal speed frames, and shooting 48 lines per frame or more in the high speed frames).

The user interface 42 permits the user to request initiation of the burst mode at any desired time, and may be implemented using any of a variety of approaches that are well known to persons skilled in the relevant arts. Examples include mechanical switches (including but not limited to pushbuttons and foot-operated switches) or virtual switches (e.g., on a touch screen).

Figure 5:
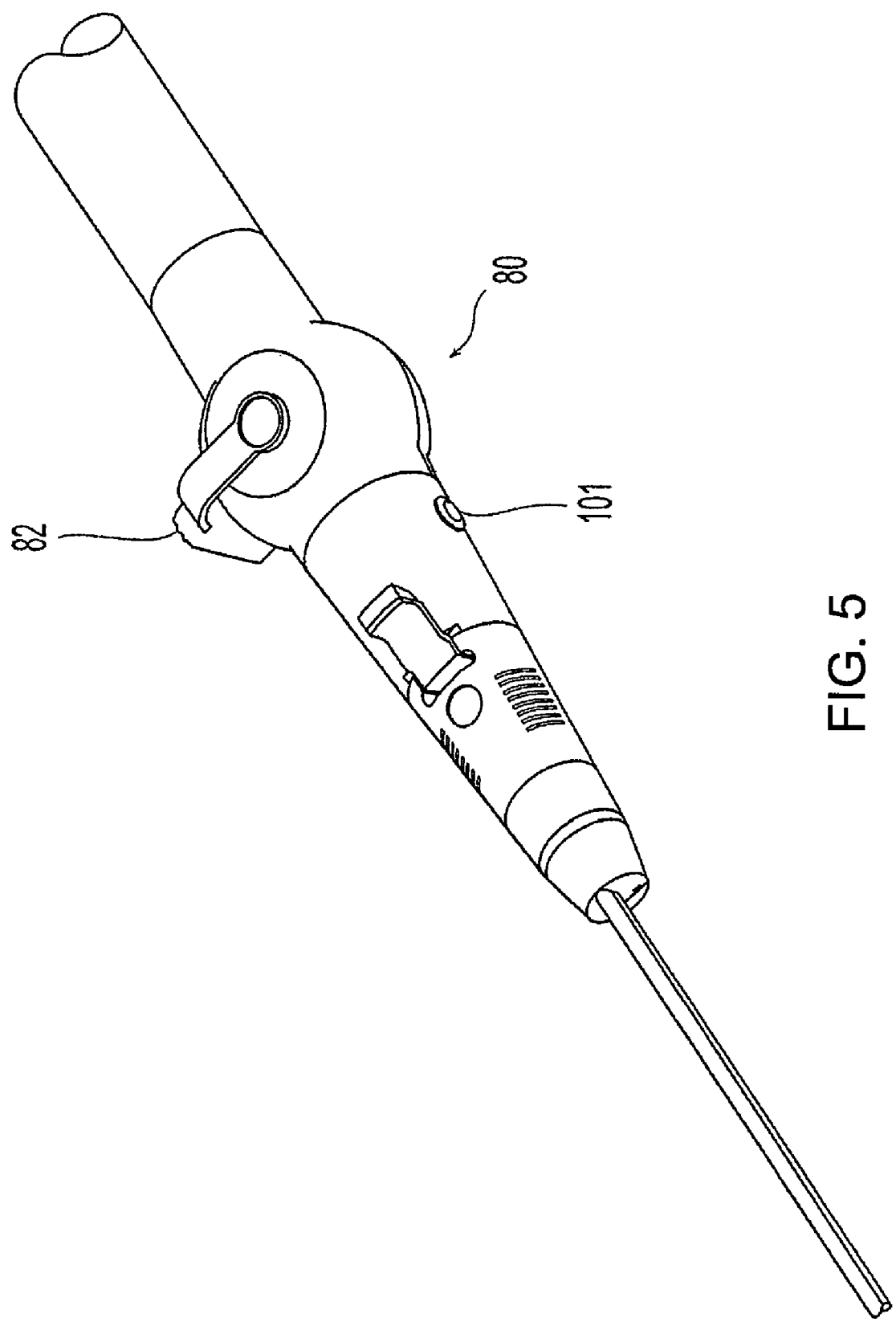
FIG. 5 depicts a handle for an ultrasound probe with a suitable user interface for requesting a temporary burst of data that is captured at a higher frame rate.

The control surface for the user interface may be located on the ultrasound console or on the probe itself. FIG. 5 depicts an embodiment in which the control button 101 is located on the handle portion 80 of the probe. When the control button 101 is pressed, the system responds by initiating the burst mode. The end of the bust mode is preferably automatically controlled by the system, and set to occur a fixed time (e.g., 3 seconds) after the burst mode began.

Note that a frame rate of 50 fps provides 20 ms time resolution. So does a sequence of averages of frames, frame 1 averaged with frame 2, frame 2 averaged with frame 3, frame 3 averaged with frame 4, etc. 20 ms is long enough for speckle from blood to "re-randomize" that is, longer than a speckle residence time, reducing the coefficient of variation of the average of an ensemble of resolution cells in the cavity (dominated by speckle which follows a Rayleigh distribution or electronic noise) in a compounded frame (compounded from two successive frames) to 71% of the similar coefficient of variation in a single frame.

Figure 3:
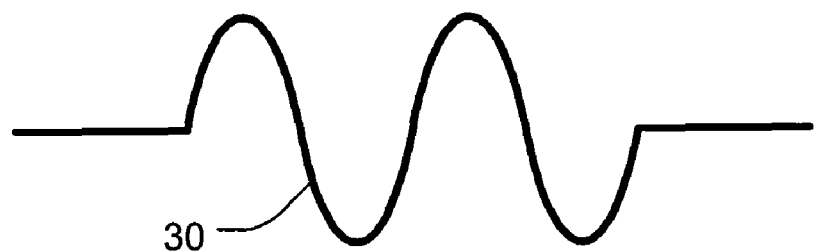
FIG. 3 is a graph of a suitable short pulse for exciting the ultrasound transducer.

Optionally, pulses with a duration of very few cycles (e.g., 1-3 cycles) may be used to excite the transducer. Since shorter pulses (in the time domain) have a relatively wide bandwidth (in the frequency domain), and attenuation in tissue is higher for higher frequency components, the low frequency components of the wide-bandwidth pulse can provide improved penetration (e.g., on the order of 10-12 cm) using a center frequency on the order of 6 MHz, without sacrificing resolution. Experimentation showed that using a two cycle pulse 30 (see FIG. 3) was optimal, especially when thermal considerations are considered (because shorter pulses will generate less heat than longer pulses of the same amplitude).

Other strategies for reducing temperature rise that may also be used to reduce power include the following: (a) making the dimensions of the transducer as large as possible consistent with a small diameter probe (b) making the frequency as low possible consistent with adequate resolution; (c) designing for thermal conductivity to spread the heat out to reduce $\Delta T$ at the hottest point on probe, e.g., as described in application Ser. No. 11/534,403, filed Sep. 22, 2006, which is incorporated herein by reference; (d) keeping the duty cycle low, consistent with acceptable image quality; and (e) using signal processing to improve the image, e.g., as described in application Ser. No. 10/997,059, filed Nov. 24, 2004, which is incorporated herein by reference.

Note that while the above-described techniques are explained in the context of TEE, the same techniques may also be use in other ultrasound imaging contexts, e.g., with probes that is inserted into cavities other than the esophagus, or probes that are applied to external surfaces of a body. Numerous modifications to the above-described embodiments will be apparent to those skilled in the art, and are also included within the purview of the invention.

We claim:

1. An ultrasound apparatus comprising:
an ultrasound imaging engine having an interface that controls a frame rate at which imaging is performed; and
a controller programmed to send commands to the imaging engine via the interface, wherein the commands cause the imaging engine to (a) set a default frame rate for imaging, (b) set, in response to an actuation of a user-actuated control, a second frame rate for imaging during a predetermined interval of time that is subsequent to the actuation, wherein the second frame rate is higher that the default frame rate, and (c) automatically reduce the frame rate to a third frame rate when the predetermined interval of time has elapsed, wherein the third frame rate is less than or equal to the default frame rate,
wherein the controller is programmed to prevent the imaging engine from operating at the second frame rate for longer than the predetermined interval of time.

2. The apparatus of claim 1, wherein imaging is performed at the third frame rate for enough time so as to compensate for the entire temperature rise caused by operating at the second frame rate.

3. The apparatus of claim 1, wherein the third frame rate is lower than the default frame rate.

4. The apparatus of claim 1, wherein the default frame rate is about 24 fps, and the second frame rate is about 50 fps.

5. The apparatus of claim 1, wherein the predetermined interval of time is less than five seconds.

6. The apparatus of claim 1, wherein the predetermined interval of time is about three seconds and imaging is performed at the third frame rate for at least seven seconds.

7. The apparatus of claim 1, wherein imaging is performed at the third frame rate for a time that is longer than the predetermined interval of time.

8. A method of performing ultrasound imaging comprising the steps of:
   (a) obtaining a first set of ultrasound image frames of a subject at a first frame rate;
   (b) switching from the first frame rate to a second frame rate in response to an actuation of a user-actuated control and obtaining a second set of ultrasound image frames of the subject at the second frame rate for a predetermined interval of time, wherein the second frame rate is higher than the first frame rate; and
   (c) preventing the step of obtaining the second set of ultrasound image frames of the subject at the second frame rate from continuing for longer than the predetermined interval of time by automatically switching from the second frame rate to a third frame rate when the predetermined interval of time has elapsed and obtaining a third set of ultrasound image frames of the subject at the third frame rate, wherein the third frame rate is less than or equal to the first frame rate.

9. The method of claim 8, wherein imaging is performed at the third frame rate for enough time so as to compensate for the entire temperature rise caused by operating at the higher frame rate during the predetermined interval of time.

10. The method of claim 8, further comprising the step of automatically switching from the third frame rate to the first frame rate and obtaining a fourth set of ultrasound image frames of the subject at the first frame rate, wherein the third frame rate is less than the first frame rate.

11. The method of claim 8, wherein the first frame rate is about 24 fps, and the second frame rate is about 50 fps.

12. The method of claim 8, wherein the predetermined interval of time is less than five seconds.

13. The method of claim 8, wherein the second predetermined interval of time is about three seconds and imaging is performed at the third frame rate for at least seven seconds.

14. The method of claim 8, wherein the imaging is performed at the third frame rate for a time that is longer than the predetermined interval of time.

15. A method of performing ultrasound imaging comprising the steps of:
   (a) obtaining ultrasound images of a subject at a first frame rate;
   (b) subsequently switching to a second frame rate that is higher than the first frame rate in response to an actuation of a user-operated control, and obtaining ultrasound images of the subject at the second frame; and
   (c) preventing step (b) from continuing for longer than a predetermined interval of time by automatically switching back to the first frame rate when the predetermined interval of time has elapsed, and subsequently obtaining ultrasound images of the subject at the first frame rate,
   wherein steps (a), (b), and (c) are all performed during a single imaging session.

16. The method of claim 15, further comprising the step of:
   (d) automatically switching to a frame rate that is lower than the first frame rate and obtaining ultrasound images of the subject at the frame rate that is lower than the first frame rate,
   wherein step (d) occurs after step (b) and before step (c).

17. The method of claim 15, further comprising the step of:
   (d) temporarily pausing imaging for less than 10 seconds,
   wherein step (d) occurs after step (b) and before step (c).

18. The method of claim 15, wherein operation at the second frame rate continues for less than five seconds.

* * * * *